United States Patent [19]

Tomantschger et al.

[11] Patent Number: 5,008,162
[45] Date of Patent: Apr. 16, 1991

[54] TEST CELL STRUCTURE

[76] Inventors: Klaus Tomantschger, 6197 Montevideo Rd., Mississauga, Ontario, Canada, L5N 2E8; Josef Soltys, 246 Third Line, Oakville, Ontario, Canada, L6L 4A1

[21] Appl. No.: 192,537

[22] Filed: May 11, 1988

[51] Int. Cl.$^5$ .................................. 429 26; 429 72; 204 400
[52] U.S. Cl. ................................................. 429/34
[58] Field of Search ................................. H01M/8/04

[56] References Cited

PUBLICATIONS

Copy of page from brochure from Prototech Corporation showing Model PCT.
Copy of page showing Micro Flow Cell from Electro Cell AB.

*Primary Examiner*—Anthony Skapars
*Attorney, Agent, or Firm*—Donald E. Hewson

[57] ABSTRACT

A test cell structure for fuel cell or electrochemical cell technology is disclosed. Principally, the test cell may be used for testing gas diffusion or solid electrodes in a controlled environment, and such other matters as quality assurance tests of fuel cell components including electrodes, electrolytes, etc. In a simple embodiment, the test cell includes a body having an electrolyte chamber extending from one side to the other, and an electrolyte reservoir above. reactant fluid (usually gas) chambers are formed in blocks that are secured to each side of the body, so that the gas chambers face the electrolyte chamber; and means are provided to conduct gas to and away from each of the gas chambers. Electrodes are mounted in interposed relation between the electrolyte chamber and the gas chambers at each side thereof, where the electrodes are mounted in a separable frame which, when in place, provides a fluidtight seal between the body and each of the respective gas chambers. in a preferred embodiment, a well is formed integrally with the body as the electrolyt reservoir, having a liquid conduit communicating to the electrolyte chamber. A gas lift pump is provided for electrolyte circulation, and to provide an inert atmosphere over the electrolye, if required. A heat exchanger may be placed into the well so as to control the operating temperature of the electrolyte.

20 Claims, 2 Drawing Sheets

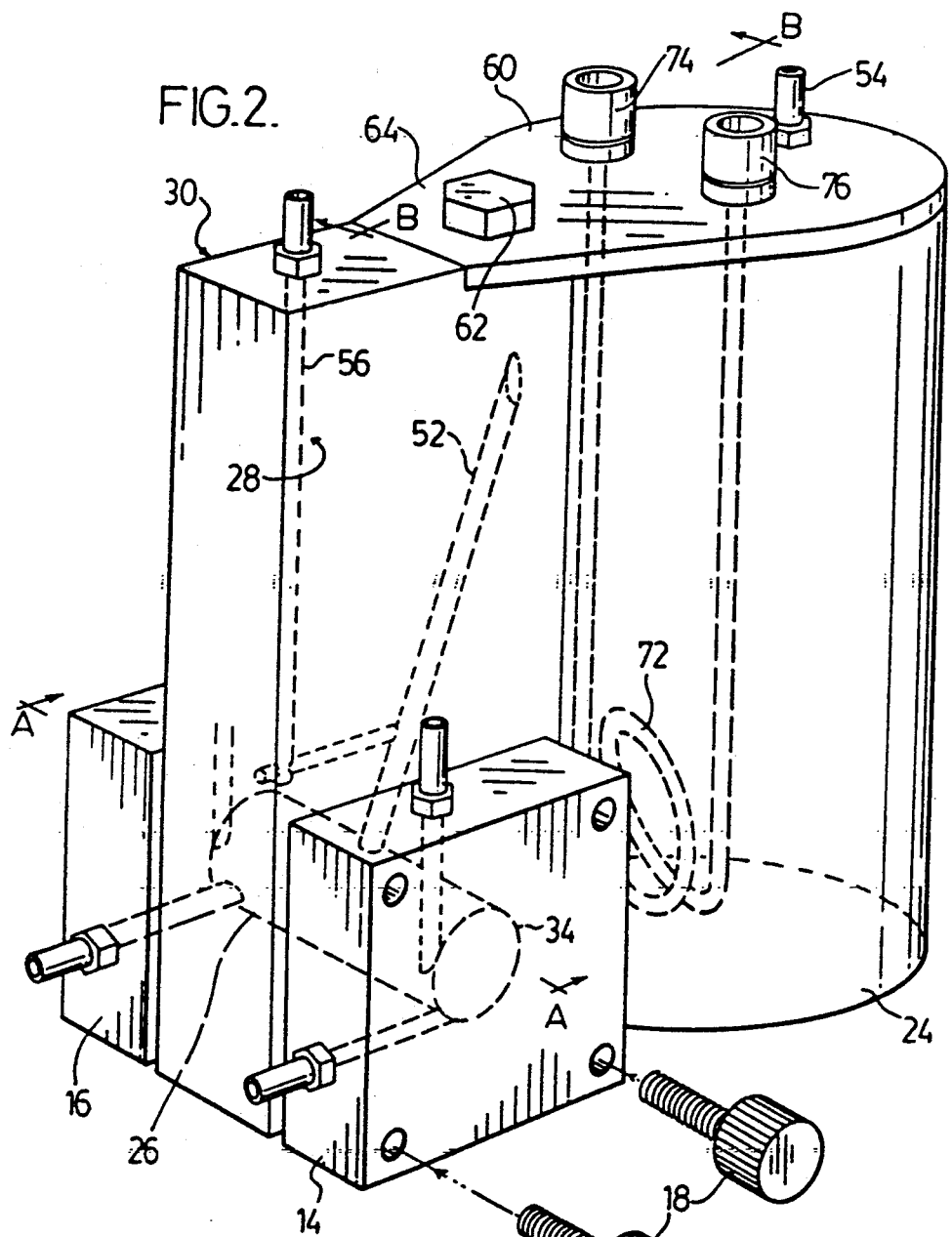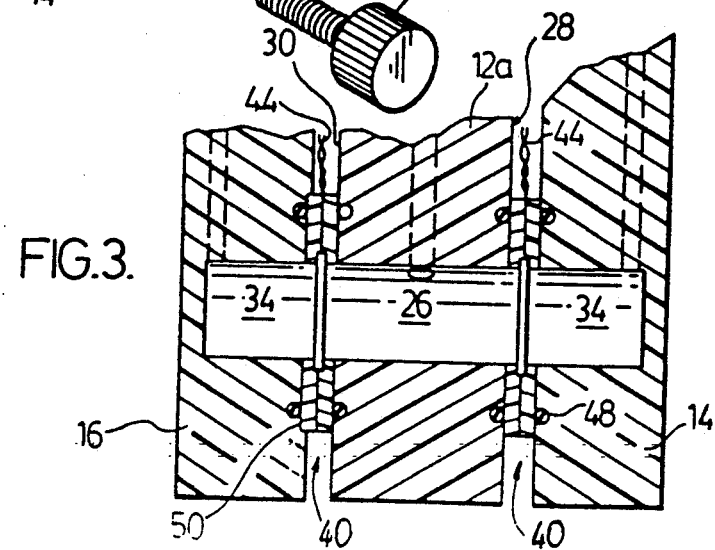

TEST CELL STRUCTURE

FIELD OF THE INVENTION

This invention relates to test cell structures intended for electrochemical cell technology, and particularly intended for fuel cell technology, where the test cell may be easily assembled and dis-assembled for purposes of replacing and/or inspection of electrodes, or for purposes of changing electrolytes and/or reactant fluids, and other research purposes. The invention provides a test cell structure which may be adapted to a number of laboratory and/or industrial applications, where in any event, the easy assembly and dis-assembly of the test cell is a pre-requisite characteristic.

BACKGROUND OF THE INVENTION

There are a number of circumstances where a test cell may be required to determine a specific operating characteristic of a fuel or other electrochemical cell—which may have gas diffusion electrodes or solid electrodes. The cells for which the present invention is particularly intended may be generally defined or characterized as being those which require a flow of reactant fluids (either gases or liquids) and liquid electrolyte, into and away from the vicinity of the electrodes, where the an electrolyte is present on the opposite side of the electrodes to that where the reactant fluids are introduced at each electrode. Fuel cells are the type of technology to which the present test cell structure is particularly directed.

Obviously, in any such electrochemical system, there are a number of variables which may be tested for, either in a laboratory situation or in quality assurance testing in a manufacturing situation. For example, the simple teaching and demonstration of fuel cell technology may require that the demonstrator may wish to show the effect of changing one or another of the various components of the test cell—for example, changing the electrolyte or the normality of the electrolyte, changing the reactant fluids, changing the electrodes exposed to the electrolyte and the reactant fluids, and so on. Obviously, in order for any such circumstances to occur, the cell structure being utilized must be capable of being easily assembled and dis-assembled.

Still other circumstances occur which require the use of a test cell structure which is capable of easy assembly and dis-assembly. Often, in research or laboratory circumstances, and relating generally to electrochemical research, it may be important to vary the use of differing components of a system under controlled conditions. Electrodes for use in batteries, fuel cells, electrosynthesis, electrodialysis, and other related fields, require an easy way of substituting one electrode structure for another in an otherwise controlled environment. The evaluation of electrochemical processes which are being developed in a laboratory, or the components required for such processes, require a controlled environment; and for the validity of empirical results to be considered, a test cell structure and environment should be provided in which only a single component or a controlled group of components is changed at any one time.

Still further, in the manufacture of components for use in commercial fuel cells and the like—those which may be used in hospitals, laboratories, military installations, etc.—there is the requirement for quality assurance of the various components being manufactured. Thus, for example, components having known characteristics, such as electrolytes and reaction gases, may be used to test the operating characteristics of sample electrodes. A known electrochemical couple between the gases, in the presence of a known electrolyte, may be calculated to develop a specific voltage having specific current density in an electrode sample of given thickness and surface area. By being capable of mounting an electrode sample, for example, in a frame having a given exposed area, quality assurance of the material of the electrode sample may be easily tested for.

All of the above very often require that the test cell be capable of operating in a wide range of temperatures, and moreover that the test cell be transparent at least in the reaction regions thereof so as to observe the electrochemical processes as they are carried out within the cell. Of course, given that the reaction gases on the one hand, and more particularly the electrolytes, may be highly alkaline or acidic, it is important to assure a liquid-tight sealing relationship within the test cell so as to protect the scientists working in the environment thereof, and indeed so as to protect the laboratory desks, etc. on which the test cells may be placed.

Still further, it may be required that long term testing of an electrochemical system be conducted where the temperature of the electrolyte is closely controlled. In those circumstances, it is appropriate to provide a well as an electrolyte reservoir, and to provide suitable means for controlling the circulation of the electrolyte into the electrolyte chamber of the test cell, while at the same time controlling and maintaining the temperature of the electrolyte at a predetermined value. All of these considerations are met by a test cell according to the present invention, by the simple expedient of providing a well into which a heat exchanger may be placed, and by providing electrolyte circulation means—usually a gas lift pump—to ensure appropriate electrolyte circulation at a controlled rate.

Thus, the present invention provides for a test cell structure for fuel cell technology and the like, which is capable of easy assembly and dis-assembly, and which assures fluid-tight sealing relationship between the electrolyte chamber and the reactant fluid chambers on each side of electrodes placed at the sides of the electrolyte chamber.

This present invention further provides a test cell structure having an electrolyte reservoir and an electrolyte circulation system whereby the operating temperature and the flow rate of the electrolyte may be closely controlled.

Still further, this invention provides for a test cell structure having differing mounting frames for electrodes, where in all cases the mounting frames provide the fluid-tight sealing relationship of the body of the test cell where the electrolyte chamber is located, to the blocks mounted at each side thereof—in which blocks are the reactant fluid chambers of the electrochemical system.

Several prior commercial structures have been available in the market. For example, a test cell for diffusion electrodes from Prototech Corporation, Model PTC, has been provided. However, that test cell is expensive, it requires dis-assembly of a minimum of eight fastening means for the simple replacement of an electrode, it does not provide for easy replacement of electrolyte, neither does it provide an easy means for making electrical connections to the cell to determine the electrochemical system operating characteristics. Still further, the Prototech device permits only the mounting of large-scale electrode structures (in the order of 3 inches square), which is itself fraught with danger when the electrode structures being tested are of a highly frangible or otherwise fragile nature.

The present invention, on the other hand, provides a mounting frame for the electrodes, which may be easily replaced by assembly and dis-assembly of only the respective reactant fluid chamber away from the body of the cell; and in the usual embodiment that assembly and dis-assembly is effected by fastening or unfastening not more than four threaded fastening bolts or other devices. Moreover, the present invention provides a frame having a reasonable electrode area, large enough for meaningful empirical results, but small enough that highly frangible or otherwise fragile electrode structures can be handled. In a usual embodiment, the exposed electrode area within the electrode mounting frames is 2.5 square cm.

Another device which is available in the market is manufactured by ElectroCell AB of Sweden. Most of the shortcomings of the Prototech device are present in the ElectroCell device, including especially high price and large electrode areas.

A precursor, more crudely constructed test cell structure, has been described in a paper given in May, 1986, before a meeting of the Electrochemical Society and published in the proceedings thereof, by Dr. K. Tomantschger (one of the inventors herein) and others, all of a predecesor laboratory institute to Astris Inc., the assignee of the present invention.

As noted above, the present invention generally comprises two embodiments: the first embodiment incorporates a simple electrolyte reservoir within the body of the test cell, relying primarily on convective flow within the electrolyte to promote circulation of the electrolyte to and from the electrolyte chamber; the other embodiment incorporates a well associated with the body, having a pumping arrangement for electrolyte circulation, and being such as to accommodate temperature control of the electrolyte.

BRIEF DESCRIPTION OF THE DRAWINGS

The invention will now be described in association with the accompanying drawings, which show two embodiments and variations thereof, and in which:

FIG. 2 is a perspective view of a second preferred, embodiment of the invention;

FIG. 3 is a partial cross section taken in the direction of arrows A—A in FIG. 2.

DESCRIPTION OF THE PREFERRED EMBODIMENTS

Generally, the present invention comprises a test cell structure for fuel cell and electrochemical cell technology, having a pair of electrodes, and being capable of easy assembly and dis-assembly, where the test cell is of the type which requires a flow of reactant fluids which may be either gases or liquids and which are conducted into and away from the vicinity of the electrodes, and having a liquid electrolyte. The cell comprises a body having two opposed side faces with an electrolyte chamber extending therebetween, and an electrolyte reservoir in fluid communication with the electrolyte chamber. A pair of reactant fluid chamber blocks is adapted for mounting to the body, one at each of the two opposed side faces thereof. Each of the reactant fluid chamber blocks has a cavity formed in a first face thereof, which cavity is opened at a first face, and closed away therefrom, so as to form a reactant fluid chamber adapted to face the end of the electrolyte chamber at each side face of the body to which the reactant fluid chambers are mounted. Discrete means are arranged for conducting reactant fluid to and away from each of the reactant fluid chambers. An electrode mounting assembly is provided for mounting a pair of substantially planar electrodes in interposed relation between the reactant fluid chambers and the electrolyte chamber, one at each side of the body. The electrode mounting means each comprises a frame into which an electrode member may be placed, and having substantially fluid-tight sealing relationship with the body and the reactant fluid chamber blocks when the blocks are securely mounted to the body at each side thereof.

Moreover specifically, there are several embodiments of the test cell according to the present invention, two general embodiments being a simple embodiment having an electrolyte reservoir, usually for short-term testing; and a more complicated structure having an integral well and electrolyte pumping means for longer term testing, or for use in circumstances where the operating temperature of the electrolyte may be a requisite characteristic.

Figure 1:
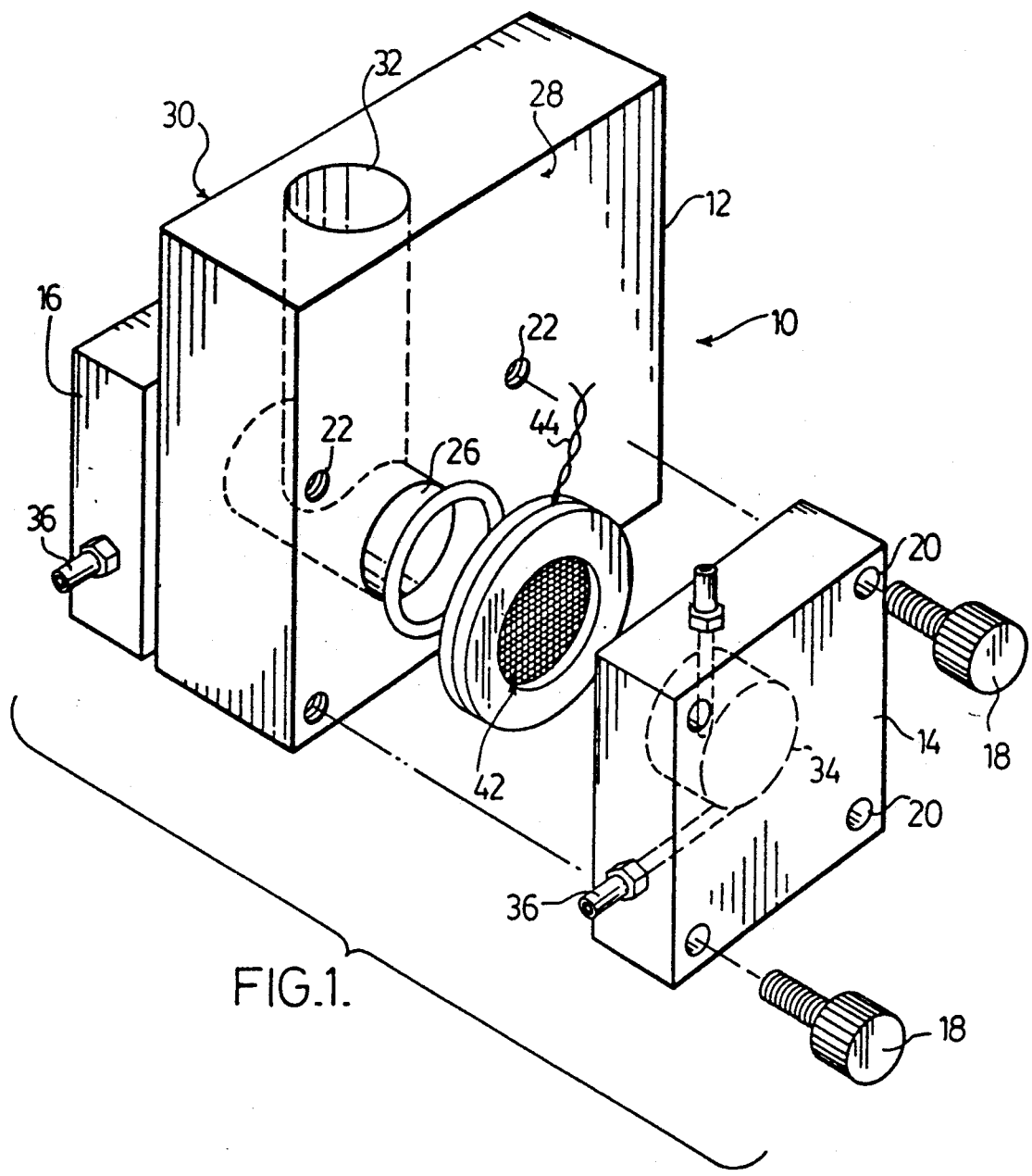
FIG. 1 is a partially exploded view of a first, simple, preferred embodiment of the invention.

FIG. 1 shows a relatively simple structure 10, having a body 12 and a pair of side blocks 14 and 16. Each of the side blocks 14 and 16 is adapted for mounting to the side of the body 12, using such means as threaded fasteners 18 which pass through openings 20 in the blocks 14 and 16, and which are received in tapped openings 22 in the side faces of the body 12. The blocks 14 and 16 are identical in both embodiments, shown in FIGS. 1 and 2, the difference being that the embodiment of FIG. 2 includes a well 24 which is integrally formed with the body 12a, as discussed hereafter.

In general, it has been found that assembly and dis-assembly of the blocks 14 and 16 to the body 12 or 12a is effected simply by finger tightening the knurled or winged ends of the fasteners 18. The usual embodiments, as shown, are that the blocks 14 and 16 are substantially square, with the openings 20 and the mating tapped holes 22 in the body 12 or 12a evenly spaced around the block, so as to apply substantially equally distributed clamping force between the blocks 14 and 16 and the body 12 or 12a, and against the interposed electrode frame as discussed hereafter.

Within the body 12 of FIG. 1, or 12a of FIG. 2, there is disposed an electrolyte chamber 26. The electrolyte chamber 26 extends from the two opposed side faces 28 and 30 of each of the bodies 12 or 12a, and thus the electrolyte chamber 26 essentially comprises a through bore or opening through the thickness of the body 12 or 12a, as best seen in FIG. 3. In the embodiment of FIG. 1, an electrolyte reservoir 32 is formed in the body 12, in fluid communication with the electrolyte chamber 26. Typically, the reservoir 32 is a cavity that is formed within the body 12 and extends from the top base thereof towards and in fluid communication with the electrolyte chamber 26.

In each of the blocks 14 and 16 there is a reactant fluid chamber 34, which is a cavity formed in the one face of each of the blocks 14 and 16 which is adapted to face the side faces 28 or 30 of the body 12 or 12a. Thus, the cavity 34 or reactant fluid chamber is open at that first defined face of each of the blocks 14 and 16, and is closed away from that face, so as to form the reactant fluid chambers 34 as defined. Each of the reactant fluid chambers 34 is adapted to face one or the other of the ends of the electrolyte chamber 26, at the respective side face 28 or 30 of the body 12 or 12a.

Discrete means are arranged in each of the blocks 14 and 16 for conducting reactant fluid to the reactant fluid chamber 34, and away therefrom. Thus, each of the blocks 14 and 16 has a first spigot 36 in the front face thereof, and a second spigot 38 in the top face thereof, as best seen in FIG. 1. Each of the spigots 36 and 38 is adapted for fluid communication by an internal conduit within the blocks 14 and 16 to the reactant fluid chamber 34 of that block, as shown in dashed lines in FIG. 1. It will be seen that, by virtue of the reactant fluid chamber 34, and the spigots 36 and 38 formed in the blocks 14 and 16, the blocks are handed—that is, a left-hand block and a right-hand block—although they are otherwise identical in structure. Of course, other mounting arrangments and placements of the spigot 36 and 38 can be made, for example by rotating the orientation of one of the blocks 90 degrees, so that a single-handed block may be used on either side of the body 12 or 12a; provided that it is not important for the ingress or egress spigots for each of the reactant fluid chambers 34 to be physically located at the front or the top faces of the blocks, in all instances.

The electrode mounting means for the test cell comprises a frame 40. Generally, the frame 40 has two side pieces between which an electrode member may be placed. Each of the frames 40 has a centrally located opening 42 therein, having a predetermined and standard dimension (typically, having a projected area of 2.5 square cm.). Thus, the use of a test cell according to the present invention assures that a known electrode area will be exposed both to the electrolyte within the electrolyte chamber 26 and to the respective reactant fluid in the respective reactant fluid chamber 34. The electrode frames 40, as noted hereafter, may be of a relatively hard material or a relatively compressible material. Indeed, the frames 40 may be cast or moulded about the electrode material placed therein.

It is worth noting, at this stage, that the relatively small projected area of the electrode at the opening 42 in the electrode frames 40 permits handling of electrode materials that may be quite frangible or otherwise fragile. In any event, the electrode is placed within the frame between the two opposed side pieces thereof, or cast or moulded thereinto; and a pigtail 44 may be soldered or otherwise connected to or placed within the frame for electrical connection to the electrode material, for purposes of leading electrical current away from the electrodes and for reading voltage between the electrodes.

The materials of the electrode frames may vary, depending on the circumstances in respect of which any particular test may be being carried out. For example, long term testing, or testing where electrodes may require to be handled a significant number of times as the cell may be assembled and dis-assembled for other purposes, usually dictate that the material of the electrode frames is a relatively hard and robust material. Typically, the two side pieces of the electrode frames 40 may, in those circumstances, be a cast or machined epoxy resin, and they may indeed be formed so as to provide a compression fit against the electrode material by having a recess in one of the two side pieces and a mating extension in the other other two side pieces between which the electrode material would be captured. Usually, in such circumstances, a slit is provided radially within one of the side pieces to permit the pigtail 44 to be placed therein for easy access, for instrumentation or electrical connection purposes. Otherwise, the electrode frame may be moulded but more usually cast about the edges of the electrode material.

Alternatively, the material of the electrode frames 40 may be a slightly compressible, closed cell foamed plastic material, such as polyethylene, polyurethane, etc. That nature of electrode frame is used where the electrode and its frame may be disposed of after a single or relatively few assembly and disassembly operations of the test cell.

In general, the reactant fluid at each side of the test cell is a gas, but since the tests cell may be used for other purposes such as electrodialysis, the structure contemplates that the reactant fluids may be liquid. The electrolyte, in any event, is a liquid.

Obviously, the material of the body 12 or 12a, the electrode frames 40, and the reactant chamber blocks 14 and 16, must all be such as to be resistant to degradation upon exposure to or contact with concentrated acids or bases. A typical electrolyte, for example, in a fuel cell having air and hydrogen or oxygen and hydrogen as the reactant gases, may be 12 N KOH—a highly alkaline substance. Other electrolytes, or reactant fluids, may be highly acidic; and in all instances, it is important that the assembly of the cell structure be essentially liquid-tight to preclude inadvertent leakage of the electrolyte and reactant fluids, especially reactant liquids.

Suitable materials, therefore, for the structure of the test cell include epoxy resin, which may be cast, machined, or cast and machined; and other suitable materials may include acrylic resins, and such other mouldable thermoplastics as high impact polystyrene, polyproplene, and the like. It is desirable, however, that in all instances the material of the body 12 or 12a, and of the blocks 14 and 16, be transparent or at least translucent so that the reaction occuring within the test cell may be observed.

The material of the fasteners 18 may typically be nylon. The external tubing and the material of the spigots—which are generally threadably connected into drilled and tapped holes within the body 12 or 12a or the blocks 14 and 16, may be polyethylene or polypropylene. Other suitable transparent, heat-resistant plastics may be used for the test cell major components, provided that the materials are resistant to acids and bases, and will operate under a wide range of operating temperatures.

In an alternative sealing arrangement, an additional recess may be provided in the faces 28 and 30 surrounding the end of the electrolyte chamber 26, and/or in the faces of the blocks 14 and 16 in which the cavities 34 are formed, surrounding the cavity, all as indicated generally at 46 and 48 in FIG. 3. An O-ring may be placed in either or both of the O-ring recesses 46 and 48, so as to provide secondary liquid-sealing properties, especially when hard epoxy resin or other hard electrode frames 40 are employed.

Yet another alternative is to provide a very slight recess in either or both of the faces 28 and 30 and/or the cavity-containing faces of the blocks 14 and 16. In this case, the recess is of generally the same diameter as the outer diameter of the electrode frame 40, as shown at 50 in the block 16 illustrated in FIG. 3.

This is not to suggest, however, that the electrode frames need necessarily be circular; and generally, particularly in the case of closed cell foamed polyethylene electrode frames, each of the side pieces thereof i square so as to provide a slightly larger gasket surface against the body 12 or 12a and the reaction chamber blocks 14 and 16, when in interposed relation therewith.

Referring briefly to the specific embodiment of FIG. 2, the well 24 is shown as being formed integrally with the body 12a. This is generally easily accommodated by casting the material of the body 12a and the well 24, followed by such machining as may be necessary. Thus, a conduit 52 is formed within the body 12a, to provide liquid communication between the electrolyte chamber 26 and the interior of the well 24. Generally, the conduit 52 is formed so as to slope upwardly from the electrolyte chamber 26 when the cell is in its usual operating orientation, as illustrated in FIG. 2. Thus, it is a simple matter to drain the electrolyte chamber 26 when the cell is not operating, by simply tilting or tipping the entire structure and permitting the electrolyte within the chamber 26 to run back through the conduit 52 into the well 24.

Circulation of the electrolyte with the well 24 to the electrolyte chamber 26 is generally effected by pressurizing the well with a gas. That is accomplished by connecting a gas inlet tube to spigot 54; and by providing a further gas pressure and electrolyte relief conduit 56 within the body 12a in liquid communication with the electrolyte chamber 26, and in communication with the egress spigot 58 in the top thereof. Thus, a gas lift pump for electrolyte circulation is easily effected.

It should also be noted that the gas used for the gas lift pump may be selected to protect the electrolyte from the ambient in which the cell is operating. For example, with KOH electrolyte, nitrogen may be used as the gas lift pump supply gas, which creates an internal nitrogen atmosphere within the well 24, thus precluding the possibility of carbonation of the KOH due to the presence of carbon dioxide in the ambient air. Obviously, the gases may be chosen, as necessary.

Figure 4:
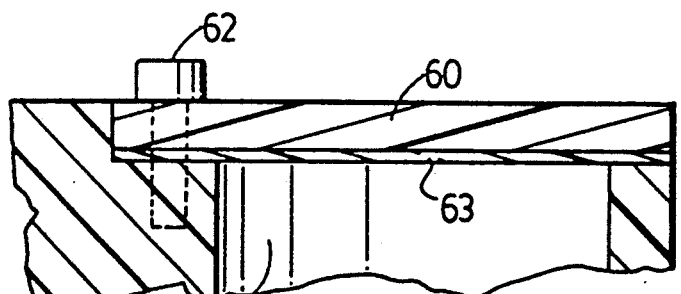
FIGS. 4 and 5 are partial cross sections of alternative embodiments taken in the direction of arrows B—B in FIG. 2.
Figure 5:
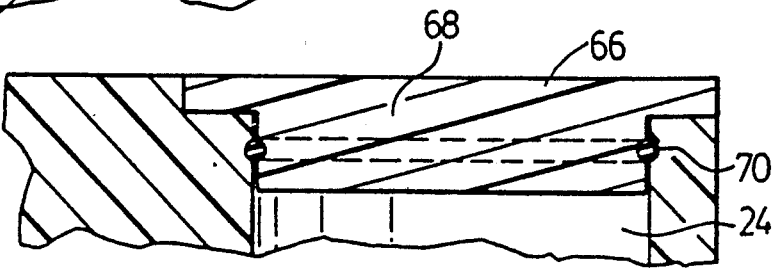

So as to seal the well 24, two alternative arrangements are shown in FIGS. 4 and 5, with reference to FIG. 2. The first alternative arrangement calls for a top piece 60 to be secured to the body 12a by a fastening means 62 such as a nylon bolt having an knurled end as shown. A gasket material 62 is placed beneath the top surface of the top piece 60 around the upper surface of the well 24; and the shape of the top piece may include the wings 64 to effect a better clamping arrangement of the top piece 60 against the gasket 62.

In the alternative of FIG. 5, the top piece 66 has an extension 68 formed in the undersurface thereof, which is sufficiently of a shape and size to extend downwardly into the well 24 at the top end of the side walls thereof. An O-ring 70 is conveniently in interposed relation between the downward extension 68 and the side walls of the well 24.

Finally, as noted in FIG. 2, a heat exchange coil 72 may be immersed within the well 24. The heat exchange coil 72 may conveniently be a hollow conduit having fluid connections 74 and 76 through the top piece 60 (or 66), so that the heat exchanger coil 72 may be connected to an external source of heated or cooled fluid—either liquid or gas—controlled in such a manner as to control the temperature of the electrolyte within the well 24. Alternatively, of course, the heat exchange coil 72 may be an electrically powered, thermostatically controlled heater. In either case, the temperature of the electrolyte within the well 24 may be electively cooled or warmed, or as required, to maintain it at a predetermined temperature or to change the temperature as the operating characteristics of the experiment being carried out may dictate.

It will be noted, upon review of the structures illustrated in FIGS. 1 and 2, that in each instance a test cell is provided which allows for the flow of reactant fluids (either gases or liquids) and of liquid electrolyte, into and away from the vicinity of the electrodes. The electrolyte is present on the opposite side of the electrodes to that where the reactant fluids are introduced at each electrode. It should also be noted that, in the case of the FIG. 1 embodiment, electrolyte flow or circulation comes as a result of convective flow within the electrolyte; whereas, in the FIG. 2 embodiment, the circulation of electrolyte comes as a result of the pumping action of the gas lift pump. In both cases, however, electrolyte circulation is provided for without any moving parts within the cell structure. This, of course, assures trouble-free operation of the cells in all instances.

There has been described a test cell structure for fuel cell technology, which clearly is adapted for easy assembly and dis-assembly, whereby various fuel cell or electrochemical components may be easily interchanged, mounted or demounted, or inspected. The assembly is such that the structure is generally translucent or transparent, and materials are suggested by which the structure will operate over a wide range of temperatures and in exposure to reactant fluids or electrolytes that may be highly acidic or basic. The embodiments shown are preferred embodiments as developed in the laboratories of the assignee corporation of the present invention, and clearly other embodiments and specific changes may be made to the test cell structure, without departing from the spirit and scope of the accompanying claims.

We claim:

1. A test cell structure for electrochemical cell technology, said test cell having a pair of electrodes, and being capable of easy assembly and dis-assembly; said test cell being of the type which requires a flow of reactant fluids, either gases or liquids, and liquid electrolyte, into and away from the vicinity of the electrodes, where said test cell structure comprises:

a body having two opposed side faces and an electrolyte chamber extending therebetween, and an electrolyte reservoir in fluid communication with said electrolyte chamber;

a pair of reactant fluid chamber blocks adapted for mounting to said body, one at each of said two opposed side faces thereof;

each of said reactant fluid chamber blocks having a cavity formed in a first face thereof, which cavity is open at said first face and closed away from said first face so as to form a reactant fluid chamber adapted to face the end of said electrolyte chamber at the side face of said body to which each respective reactant fluid chamber block is mounted;

discrete means arranged for conducting reactant fluid to and away from each of said reactant fluid chambers;

and electrode mounting means for mounting a pair of substantially planar electrodes in interposed relation between said reactant fluid chambers and said electrolyte chamber, one at each side face of said body;

said electrode mounting means each comprising a frame into which an electrode member may be placed, and having substantially fluid-tight sealing relationship with said body and said reactant fluid chamber blocks when said blocks are securely mounted to said body at each side face thereof.

2. The test cell structure of claim 1, adapted for operation when said reactant fluid for each of said electrodes is a gas, and said reactant fluid chamber at each side of said body is a gas chamber.

3. The test cell structure of claim 2, where said electrolyte reservoir is formed in said body above said electrolyte chamber, and electrolyte circulation is substantially as a result of convective flow within said electrolyte.

4. The test cell structure of claim 2, where said electrode mounting means each comprises a separable frame having two side pieces between which an electrode member may be placed.

5. The test cell structure of claim 2, where said gas chamber blocks are mounted at each side of said body by threaded means passing through said blocks and secured into said body; whereby assembly and disassembly of said test cell is effected by fastening and unfastening said threaded means, and thereby tightening and loosening said fluid-tight sealing relationship of said electrode mounting frames interposed between said body and said blocks at each side of said body.

6. The test cell structure of claim 4, where said gas chamber blocks are mounted at each side of said body by threaded means passing through said blocks and secured into said body; whereby assembly and disassembly of said test cell is effected by fastening and unfastening said threaded means, and thereby tightening and loosening said fluid-tight sealing relationship of said electrode mounting frames interposed between said body and said blocks at each side of said body.

7. The test cell structure of claim 4, where the pieces of said separable frames of said electrode mounting means are each formed of a compressible, closed-cell foamed plastics material.

8. The test cell structure of claim 4, where the pieces of said separable frames of said electrode mounting means are each formed of a relatively hard material, and a slight recess is formed in at least one of each of said side faces of said body and said first faces of said gas chamber blocks, to accommodate a portion of the thickness of each of said separable frames.

9. The test cell structure of claim 8, where the pieces of said separable frames of said electrode mounting means are each formed of a relatively hard material, and an O-ring recess is formed in at least one of each of said side faces of said body and said first faces of said gas chamber blocks, and an O-ring is placed in each such O-ring recess, to provide secondary fluid-tight sealing relationship of said electrode mounting frames interposed between said body and said gas chamber blocks at each side thereof.

10. The test cell structure of claim 5, where said electrolyte reservoir is a well which is formed integrally with said body, and having a liquid conduit formed within said body in communication between said electrolyte chamber and said well.

11. The test cell structure of claim 10, where said liquid conduit is formed so as to slope upwardly from said electrolyte chamber when said cell is in its usual operating orientation; and circulation of electrolyte from said well to said electrolyte chamber is effected by pressurizing said well with a gas; and wherein a further gas pressure and electrolyte relief conduit is also formed within said body.

12. The test cell structure of claim 11, where said well is adapted to receive a heat exchanger placed therein, and said heat exchanger is adapted for connection to an external source so as to heat or cool the liquid electrolyte within said well by heat exchange therewith.

13. The test cell structure of claim 1, where the material of each of said body and said reactant fluid chamber blocks is a transparent plastics material.

14. The test cell structure of claim 10, where said heat exchanger is in the form of a fluid conducting tube adapted to conduct a fluid that may be electively cooler or warmer than said electrolyte, so as to maintain the temperature thereof at a predetermined level.

15. The test cell structure of claim 11, where said heat exchanger is a thermostatically controlled electrically powered heater.

16. The test cell structure of claim 13, where the material of said body and said reactant fluid chamber blocks is chosen from the group consisting of cast and machined epoxy resins and acrylic resins, and mouldable high impact polystyrenes and polypropylenes.

17. The test cell structure of claim 11, where said well is liquid sealed at the top thereof by a top piece secured to said body, and having a gasket member interposed between said body and the underside of said top piece around the top edge of said well.

18. The test cell structure of claim 11, where said well is liquid-sealed at the top thereof by a top piece having a downward extension thereof of a shape and size to be accommodated by the inner side walls of said well near the top thereof, and by an O-ring in interposed relation between said downward extension and said side walls.

19. The test cell structure of claim 11, where the gas for pressurizing said cell is an externally supplied gas, and may be an inert gas which is non-reactive with said liquid electrolyte.

20. The test cell structure of claim 11, where the gas for pressurizing said well is one of the reactant gases of said cell.

* * * * *